(12) United States Patent
Eikelmann et al.

(10) Patent No.: US 8,537,352 B2
(45) Date of Patent: Sep. 17, 2013

(54) CUVETTE, INSERT, ADAPTER AND METHOD FOR OPTICALLY EXAMINING SMALL AMOUNTS OF LIQUID

(75) Inventors: Sven Eikelmann, Hamburg (DE); Christoph Jolie, Hamburg (DE); Wolfgang Goemann-Thoss, Hamburg (DE)

(73) Assignee: Eppendorf AG, Hamburg (DE)

( * ) Notice: Subject to any disclaimer, the term of this patent is extended or adjusted under 35 U.S.C. 154(b) by 203 days.

(21) Appl. No.: 12/933,782

(22) PCT Filed: Mar. 23, 2009

(86) PCT No.: PCT/EP2009/002114
§ 371 (c)(1),
(2), (4) Date: Mar. 21, 2011

(87) PCT Pub. No.: WO2009/115344
PCT Pub. Date: Sep. 24, 2009

(65) Prior Publication Data
US 2011/0164245 A1 Jul. 7, 2011

Related U.S. Application Data

(60) Provisional application No. 61/038,596, filed on Mar. 21, 2008.

(51) Int. Cl.
*G01N 1/10* (2006.01)
(52) U.S. Cl.
USPC ........................................................ 356/246
(58) Field of Classification Search
USPC ........................................................ 356/246
See application file for complete search history.

(56) References Cited

U.S. PATENT DOCUMENTS

| | | | |
|---|---|---|---|
| 4,682,890 A | | 7/1987 | de Macario et al. |
| 5,285,253 A * | | 2/1994 | Kloth ............................ 356/246 |
| 5,331,398 A | | 7/1994 | Eggl et al. |
| 5,601,991 A | | 2/1997 | Oberhardt |
| 5,795,748 A | | 8/1998 | Cottingham |
| 6,249,345 B1 * | | 6/2001 | Kraack et al. ................. 356/246 |
| 2002/0116897 A1 | | 8/2002 | Higashizaki et al. |
| 2002/0140931 A1 | | 10/2002 | Robertson |
| 2006/0077390 A1 | | 4/2006 | Kralik |
| 2006/0109468 A1 | | 5/2006 | Evans |
| 2007/0019189 A1 | | 1/2007 | Marsteller et al. |

FOREIGN PATENT DOCUMENTS

| | | |
|---|---|---|
| DE | 2726498 A1 | 12/1978 |
| DE | 19826470 A1 | 12/1999 |
| JP | 2007-271560 A | 10/2007 |
| WO | 9936764 A1 | 7/1999 |
| WO | 0075632 A1 | 12/2000 |
| WO | 2005114146 A1 | 12/2005 |
| WO | 2006086459 A2 | 8/2006 |
| WO | 2007-111838 A2 | 10/2007 |
| WO | 2007111555 A1 | 10/2007 |

* cited by examiner

*Primary Examiner* — Tu Nguyen
(74) *Attorney, Agent, or Firm* — Vidas, Arrett & Steinkraus

(57) ABSTRACT

A cuvette comprising at least one insert with two measuring surfaces, wherein the insert is a measurement tip, which has the two measuring surfaces on one end, which is distanced from another end of the measuring tip, and an adapter for insertion in a cuvette shaft of an optical measuring device and means of insert and adapter for releasably holding the at least one insert in the adapter with the measuring surfaces at a separation distance from each other for the positioning of a sample between the measuring surfaces in a beam path of the optical measuring device passing through the cuvette shaft.

19 Claims, 13 Drawing Sheets

CUVETTE, INSERT, ADAPTER AND METHOD FOR OPTICALLY EXAMINING SMALL AMOUNTS OF LIQUID

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to the analysis of liquid samples with a spectrometer or photometer or other optical measuring devices. Such analyses take place typically, but not exclusively, in molecular biological, biochemical, inorganic chemistry, organic chemistry and food chemistry laboratories. Samples are analyzed optically e.g. in research, diagnostics and quality control. They are analyzed e.g. by means of absorption, reflection, emission, fluorescence, Raman or luminescence spectroscopy in the UV-VIS or IR wavelength range. Examples for analytes to be measured are biomolecules like nucleic acids, proteins, lipids as well as inorganic or organic substances and compounds. These analytes can be measured directly or after a chemical reaction, which serve to facilitate spectrometric or photometric analysis.

The invention relates in particular to all exemplary applications. An important area of application is the measurement of valuable samples in small amounts in molecular biology. In many cases, only small sample amounts (e.g. below 1 to 5 microliters) are available because no more material can be obtained. Thinning of the samples would lead to measurement results that are too inaccurate due to reduced absorptions. A typical application is the photometric or fluorometric measurement of nucleic acid concentrations before a PCR or real-time PCR in order to be able to use them for the PCR optimal output amount of the nucleic acid. Another example is the measurement of the concentration of nucleic acids and marker substances built into the nucleic acids and the marking density derived from it in the case of marked nucleic acids, in order to be able to use the optimal amount of the marked nucleic acid before the start of a microarray experiment and to be sure that the marking density of the nucleic acid lies in the optimal range.

BRIEF SUMMARY OF THE INVENTION

Liquid samples are filled in cuvettes for spectrometric or photometric analysis. Standard cuvettes are suitable for insertion into the cuvette shafts of most prevalent spectrometers and photometers. These cuvette shafts are also called "standard cuvette shafts" below. Standard cuvette shafts of commercially available optical measuring devices with a cross-section of 12.5 mm×12.5 mm have become widely used. The heights of the light beam above the bottom of the cuvette shaft vary by 8.5 mm to 20 mm depending on the device. Standard cuvettes have a box-shaped profile, wherein the cross-section and the height are adjusted for the dimension of the standard cuvette shafts.

Reusable standard cuvettes made of quartz glass for small sample amounts are sold in particular by the companies Hellma and Strana. These ultra-micro cuvettes have a layer thickness of 1 mm or more. They are very difficult to fill bubble-free and extremely complex to empty and clean. Since the main applications of the optical measurements of very small volumes lie in the measurement of nucleic acids in the UV range, they are made of quartz glass and are particularly expensive. Since they are very expensive to acquire, they must be handled carefully. For ultra-micro cuvettes offered in the market made of quartz glass, a minimum volume of 5 microliters must be used, which is too much for some applications.

Other cuvettes are sold under the name "microliter measurement cell." The company Hellma markets a microliter measurement cell under the product name "Tray Cell®" and the company Implen under the product name "Label Guard," the dimensions of which are the same as a standard cuvette and can thus be used in many prevalent spectrophotometers. The microliter measurement cell made by Hellma is described in WO 2005/114146 A1. In order to perform the analysis, a drop of the liquid to be analyzed of approx. 1 to 2 microliters in the case of a layer thickness of 0.2 mm or respectively 3 to 5 microliters in the case of a layer thickness of 1 mm must be applied to the top side of a measurement window. The measurement chamber is closed by a lid. The light beam of the measurement optics is guided via beam deflections and fiber-optic light conductors and a mirror in the lid from the radiation source through the sample to the sensor.

The microliter measurement cell is constructively very complex and has a high price and is thus not always economically viable. Moreover, it has a high device-dependant self-absorption of approx. 1.3 E at 230 to 650 nm, by which the measurement range of the measuring device is reduced. Furthermore, there is no visual verifiability of the measurement solution in the measurement chamber after the sample filling and the lid fitting, in order to be able to identify e.g. disruptive bubbles, particles and incorrect pipetting, which can lead to incorrect measurements. It is also disadvantageous that the user must extensively clean the measurement window after use.

The company NanoDrop Technologies markets a photometer under the product name "NanoDrop®" that enables analysis of samples with a volume of just one microliter. The spectrophotometer is described in WO 2006/086459 A2. The system provides for the direct optical measurement in a liquid drop that is located between two horizontally arranged, planar surfaces. A light source illuminates the liquid sample from the side through the gap between the two surfaces. A fiber-optic light conductor that transfers the light to a fiber-optic spectrophotometer after passing through the sample liquid empties into the lower surface. The sample liquid is thus in direct contact with the fiber glass.

It is disadvantageous on the spectrophotometer that the optical surface can be impaired by certain samples. According to the operating instructions for the NanoDrop-1000 spectrophotometer, these are e.g. protein-containing solutions. In this case, the user must recondition the optical surface manually after multiple uses through intensive, tedious, heavy rubbing. Strongly acidic or alkaline solutions can also not be used.

Furthermore, the sample is in direct, open contact with the environment. Hazardous substances can thus not be examined with this system. However, hazardous substances, like potentially infectious substances, are frequently used in molecular biological, cell biological, biochemical and chemical laboratories. The system is not suitable for these samples. Due to the open contact of the sample with the environment, samples can be contaminated. This can falsify the measurement. Moreover, a recovery of valuable samples after the measurement is not possible without risk of contamination.

The spectrophotometer is a very expensive measurement system. It comprises a measuring unit and a PC and takes up a lot of space. The sample can evaporate quickly and be contaminated easily because the lateral surface of the open liquid drop is in direct contact with the environment.

Based on this, the object of the invention is to provide a device that is suitable for optical examination of a small sample amount with high accuracy by means of conventional optical measuring devices.

Furthermore, a method enabling the optical examination of particularly small sample amounts should be provided.

The object is solved through a cuvette with the characteristics of claim 1. Advantageous embodiments of the cuvette are specified in the dependent claims.

The cuvette according to the invention comprises at least one insert with two measuring surfaces and an adapter for insertion into a cuvette shaft of an optical measuring device and means for the releasable holding of the at least one insert in the adapter with the measuring surfaces at a distance from each other for the positioning of a sample between the measuring surfaces in a beam path of the optical measuring device passing through the cuvette shaft.

The two measuring surfaces are arranged on one end of a measurement tip, which is distanced from another end of the measurement tip. The measuring surfaces are preferably integrally connected with the measurement tip. In accordance with one embodiment, the measurement tip can be positioned in an adapter with the measuring surfaces in vertical alignment in the cuvette shaft.

In accordance with one embodiment, the other end is designed such that it can be connected with a pipette, i.e. like the upper end of a pipette tip (e.g. in that it has a fitting opening, which can be fitted on the corresponding (e.g. cylindrical or conical) appendage of a pipette). In this embodiment, the measurement tip is also called a "pipette tip" below. In the design as a pipette tip, the measurement tip can be fitted on a pipette analogous to a conventional pipette tip and used for receiving the medium to be measured. The pipette to be used can be a conventional pipette, but can also be designed especially for this application. For this, it can comprise in particular an optical measuring device, the beam path of which runs between the two measuring surfaces that are located on the bottom end of the measurement tip. In accordance with another embodiment, the measurement tip is designed such that it can be connected with a (dosage) tool. In this embodiment, the measurement tip can be fitted on a tool, which has no dosing function or only an incomplete dosing function (e.g. only the receiving or only the releasing of liquid between the measuring surfaces) or a complete dosing function. Even in this embodiment, the measurement tip can have an upper end (e.g. with fitting opening) like a conventional pipette tip. In the case of a tool without a receiving function, the receiving of liquid can take place through hydrostatic pressure (immersion of the measuring surfaces) and/or capillary force. For this, in accordance with one embodiment, one or both measurement surfaces are hydrophilic or hydrophilized. The receiving of liquid through capillary force can also generally take place without an additional tool in that the measurement tip is held directly by the user. For this, the body of the measurement tip can be designed as a handle.

In the case of a tool without the releasing function of a pipette, the release of the liquid cannot take place with a defined volume like in the case of a pipette but rather for example through release on an absorbent material, which largely removes the liquid from the measurement tip, or through the discharge of all liquid. The release can take also place without a tool if applicable. For this, the body of the measurement tip can be designed as a handle.

In accordance with another embodiment, the other end of the measurement tip has means for gripping (e.g. a knob, catch or other handle). In this embodiment, the receiving of liquid can take place through hydrostatic pressure (immersion of the measuring surfaces) and/or capillary force. The release can also take place on absorbent material. Additionally, the other end of this measurement tip can be designed like the upper end of a pipette tip so that it is fillable and dischargeable like a pipette tip by means of a pipette.

The adapter has a shape fit for a cuvette shaft so that a sample held between the measuring surfaces of the insert is arranged in the beam path if the insert is inserted into the adapter and the adapter is inserted into the cuvette shaft.

A preferred embodiment has means for positioning the two measuring surfaces in a standard cuvette shaft. A standard cuvette shaft in terms of this application has a rectangular, in particular quadratic, cross-section. In accordance with one embodiment, it has a surface area of 12.5 mm×12.5 mm. In accordance with another embodiment, the beam path runs at a separation distance of 8.5 mm to 20 mm under the bottom of the cuvette shaft. In accordance with another embodiment, the beam path runs at a separation distance of 8.5 mm or 15 mm under the bottom of the cuvette shaft. The cross-section of the adapter for receiving the insert is adjusted for the cross-section of the standard cuvette shaft. In accordance with one embodiment, the measuring surfaces are positioned in the cuvette such that their center has the above separation distance of the beam path from the bottom of the cuvette shaft.

In accordance with one embodiment, the cuvette has means for the positioning of the insert in different positions in a cuvette shaft. In accordance with other embodiments, these are means for the positioning in different height positions in the cuvette shaft. These means can be e.g. extractable or respectively unscrewable feet of the cuvette. They serve e.g. for the adjustment to the height of the beam path of the measuring device.

In terms of the invention, a cuvette is a device that is designated to position samples for optical examinations. Thus, a cuvette according to the invention does not have to be designed in the conventional manner as a vessel with a receiver for liquid surrounded by bottom and side walls, wherein however such a design is also not excluded.

In the case of the cuvettes according to the invention, a low volume of a liquid sample is positioned between the two measuring surfaces. Through the surface tension of the liquid, a column forms between the two measuring surfaces, through which an optical measurement can be performed. The adapter serves to position the measuring surfaces in preferably vertical alignment in a cuvette shaft such that the measurement can be performed without further changes to the optical path in a conventional photometer or spectrometer. For this, the adapter is preferably set to the dimensions of a standard cuvette shaft so that it can be used like a standard cuvette. But the adapter can also be set to a cuvette shaft with other dimensions than a standard cuvette shaft.

The insert and/or adapter can be designed for multiple uses or as consumable or disposable for single use. The insert and/or the adapter can be made of one or several plastics (e.g. polypropylene, polyethylene, polystyrene, PVC) and/or one single or several different materials. The adapter can also be made of metal (e.g. aluminum or stainless steel, in particular if it is designated for multi-layer use. Insert and adapter can alternatively be unreleasably connected or respectively consist of one single device.

The measuring surfaces can also alternatively be equipped such that, e.g. through corresponding surface design, several samples can be arranged on it. The samples can be different or applied to the measuring surface as identical samples.

Through different separation distances between the two measuring surfaces, measurements with volumes of under one microliter up to several microliters can be realized in a cuvette. In accordance with one embodiment, the separation distances between the measuring surfaces are measured such that samples with volumes of 0.5 to 5 microliters can be held between the measuring surfaces. The separation distances between the measuring surfaces are preferably measured such that samples of approximately 1 to 3 microliters can be held. The cuvette can thus be designed for a certain volume, wherein the measuring surfaces can only be held at a certain separation distance from each other in the beam path.

An insert according to the invention for an adapter insertable into a cuvette shaft of an optical measuring device has two measuring surfaces and means for holding on the adapter with the measuring surfaces at a separation distance from each other for the positioning of a sample between the measuring surfaces in a beam path of the optical measuring device passing through the cuvette shaft. The insert is thereby a measurement tip, which has the two measuring surfaces on one end, which is distanced from one end of the measurement tip for connection with a pipette.

The means for releasable holding of the insert can be in particular contours or respectively an outer geometry of the insert, which is set to a contour or respectively geometry of the adapter so that the insert can be joined with the adapter.

The insert according to the invention can advantageously have one or more characteristics of the insert of the cuvette according to the invention described previously, which comprises at least one insert and one adapter.

An adapter according to the invention for at least one insert with two measuring surfaces can be inserted into a cuvette shaft of an optical measuring device and has means for the releasable holding of the at least one insert with the measuring surfaces at a separation distance from each other for the positioning of a sample between the measuring surfaces in a beam path of the optical measuring device passing through the cuvette shaft.

The adapter according to the invention can advantageously have one or more characteristics of the adapter of the cuvette according to the invention described previously, which comprises at least one insert and one adapter.

The means for the releasable holding of the adapter can be in particular a contour or respectively geometry of the adapter, which is set to a contour or respectively geometry of an insert so that the adapter can be joined with the insert.

In the case of all previously named invention variants, the beam path of the optical measuring device can run diagonally through the measuring surface, for which the measuring surfaces or respectively the inserts with measuring surfaces are designed transparent or clear. In accordance with another embodiment, the beam path of the optical measuring device runs parallel to the measuring surfaces through open sides of the separation distance area between the measuring surfaces. The measuring surfaces can then also be designed opaque.

Measuring surfaces can generally have a bent or other shape. In accordance with a preferred embodiment, the measuring surfaces are planar. In the case of arrangement of the measuring surfaces on the side of a plate or respectively wall, both sides of the plate or respectively wall are preferably planar.

The planar measuring surfaces can generally have any alignment with respect to each other. For example, they can be aligned at an angle to each other. In accordance with a preferred embodiment, the measuring surfaces are arranged plane-parallel with respect to each other. The plane-parallel arrangement of planar measuring surfaces serves in particular for the passage of the beam path through the measuring surfaces without disruptive deflection of the light beam.

The measuring surfaces can generally have different alignments with respect to each other, for example such that the measuring surfaces assume angles with respect to each other in all three spatial axes. In accordance with a preferred embodiment, the measuring surfaces have an overlapping arrangement. The measuring surfaces are preferably present on plane-parallel plates in an overlapping arrangement.

In accordance with one embodiment, the separation distance of the measuring surfaces from each other in the measurement position is 5 mm or less. With the named separation distance, many of the liquid samples to be examined are held between the measuring surfaces due to capillary forces. The separation distance is preferably 0.1 to 2 mm.

In accordance with a method according to the invention for the optical examination of small liquid amounts, an intermediate area, e.g. between two measuring surfaces, with an opening is brought into contact with a liquid, with the help of a displacement device, e.g. a pipette, liquid is received in the intermediate space and if applicable pushed out of it and the liquid in the intermediate space undergoes an optical measurement.

A secure and handling-friendly positioning of drops can be facilitated in all invention variants through a guidance of the pipette tip during the receiving and/or releasing of the liquid.

The cuvette according to the invention is preferably designed such that it fits into a standard cuvette shaft like a standard cuvette. However, it can also be designed such that it can be inserted into a cuvette shaft of other conventional or future optical measuring devices.

DETAILED DESCRIPTION OF THE INVENTION

Figure 1:
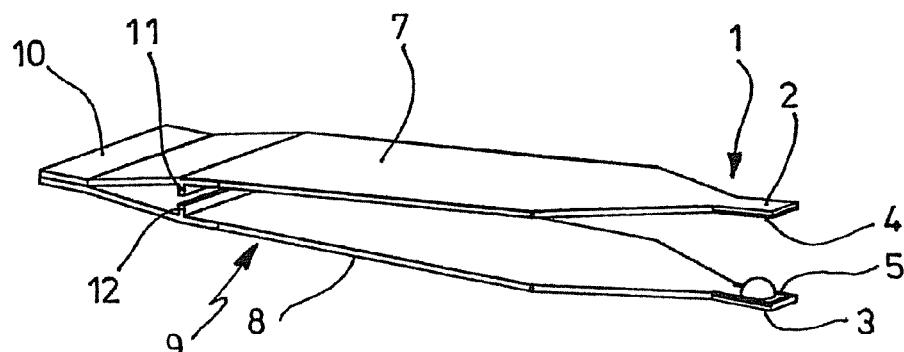
FIG. 1 Tweezers with planar measuring surfaces on the free ends and open arms in a perspective view diagonally from the side.
Figure 2:
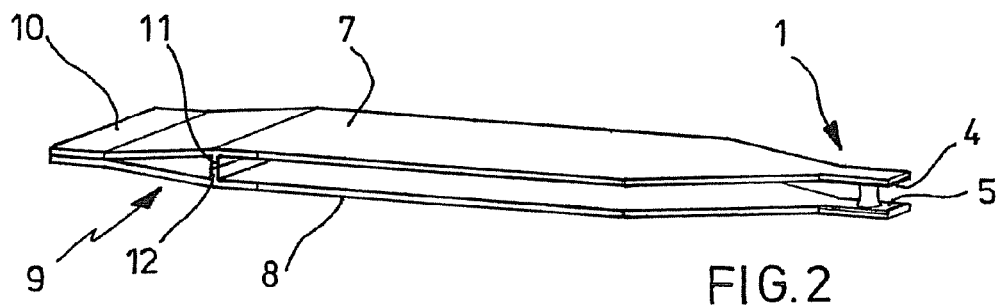
FIG. 2 the same tweezers with arms pivoted together in the same perspective view.
Figure 3:
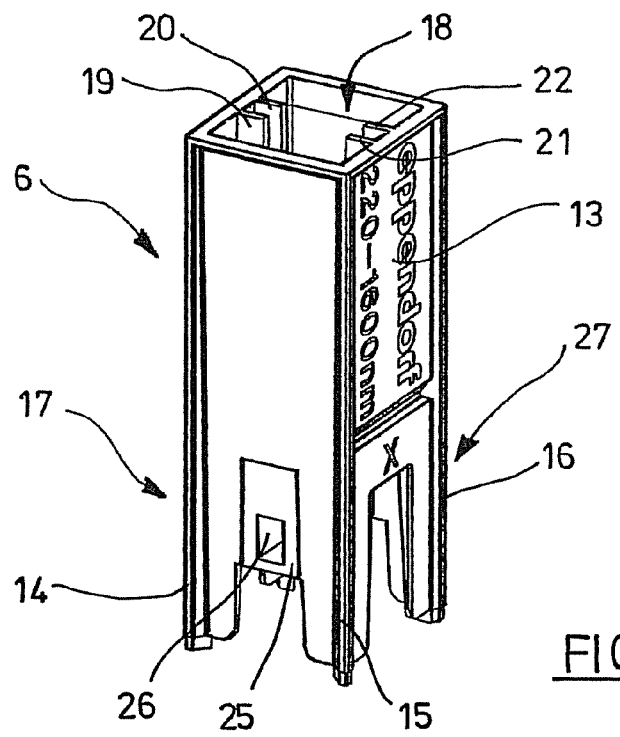
FIG. 3 an adapter with a receiver for the tweezers in a perspective view diagonally from the top and from the side.
Figure 4:
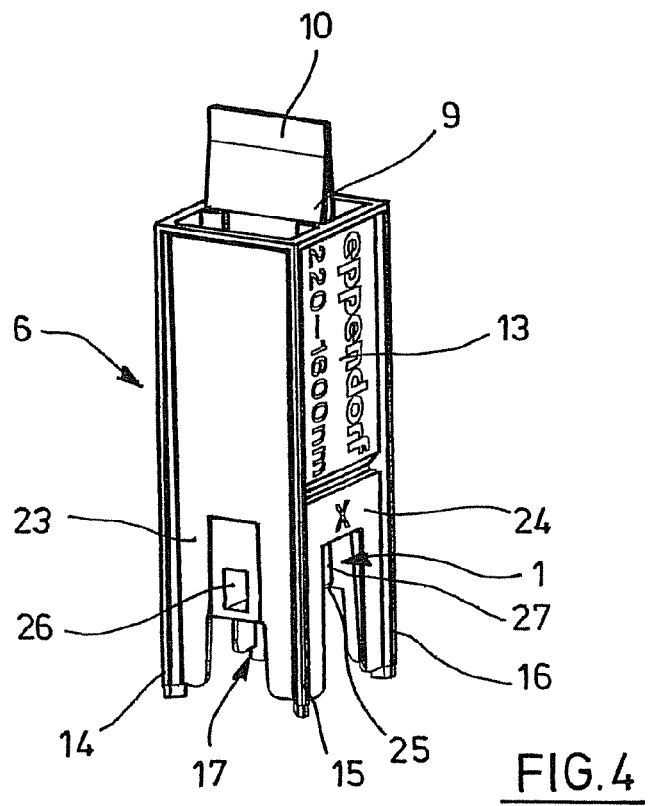
FIG. 4 the same adapter with inserted tweezers in a perspective X-ray view.
Figure 5:
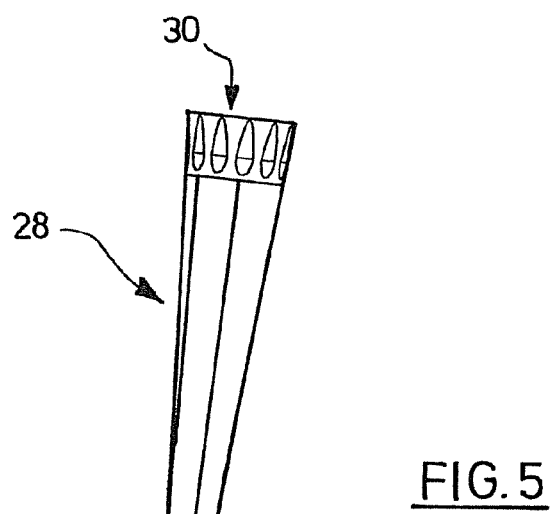
FIG. 5 a pipette tip with planar measuring surfaces on the bottom end in a perspective view diagonally from the bottom and from the side.
Figure 6:
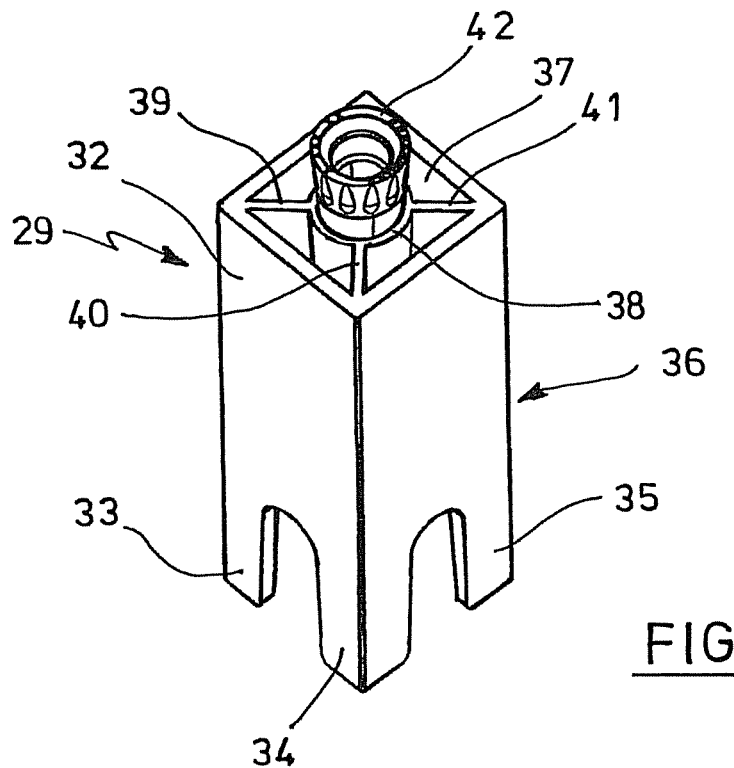
FIG. 6 an adapter with a receiver and the pipette tip inserted in it in a perspective view diagonally from the top and from the side.
Figure 7:
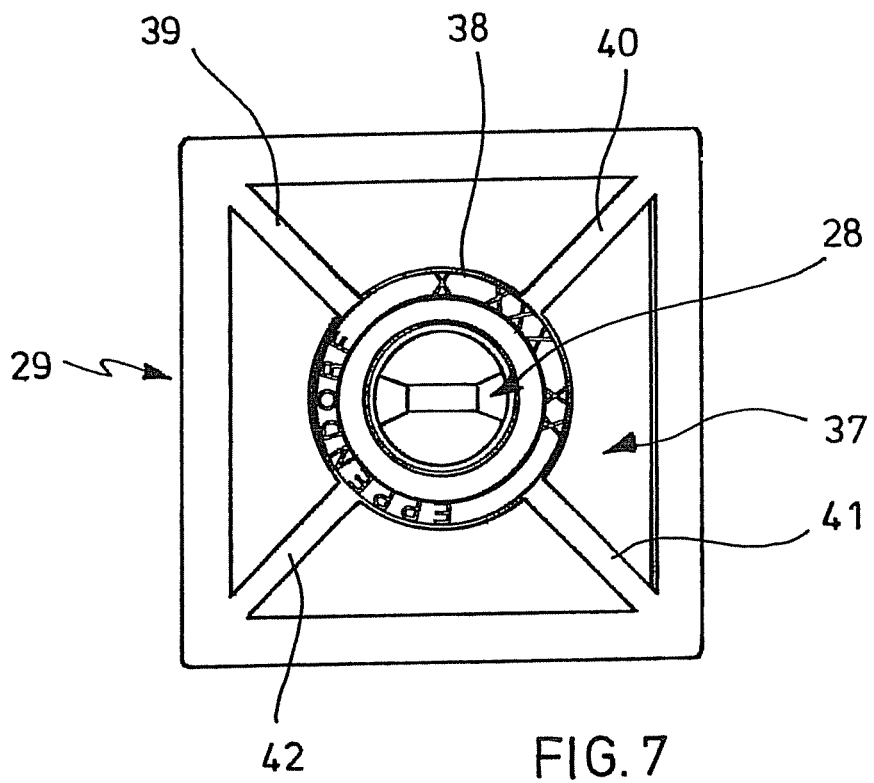
FIG. 7 the pipette tip inserted into the adapter in a top view.
Figure 8:
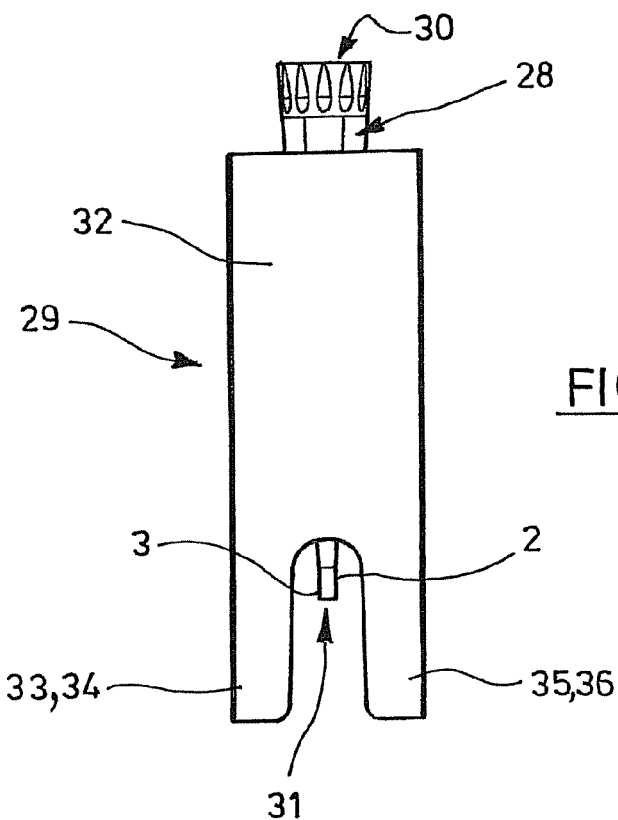
FIG. 8 the pipette tip inserted into the adapter in a side view.
Figure 9:
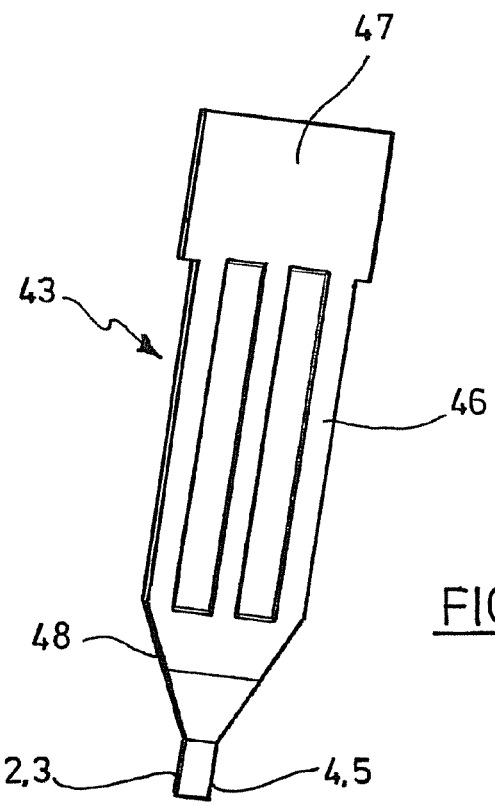
FIG. 9 a slide with a planar measuring surface in a perspective view diagonally from the top and from the side.
Figure 10:
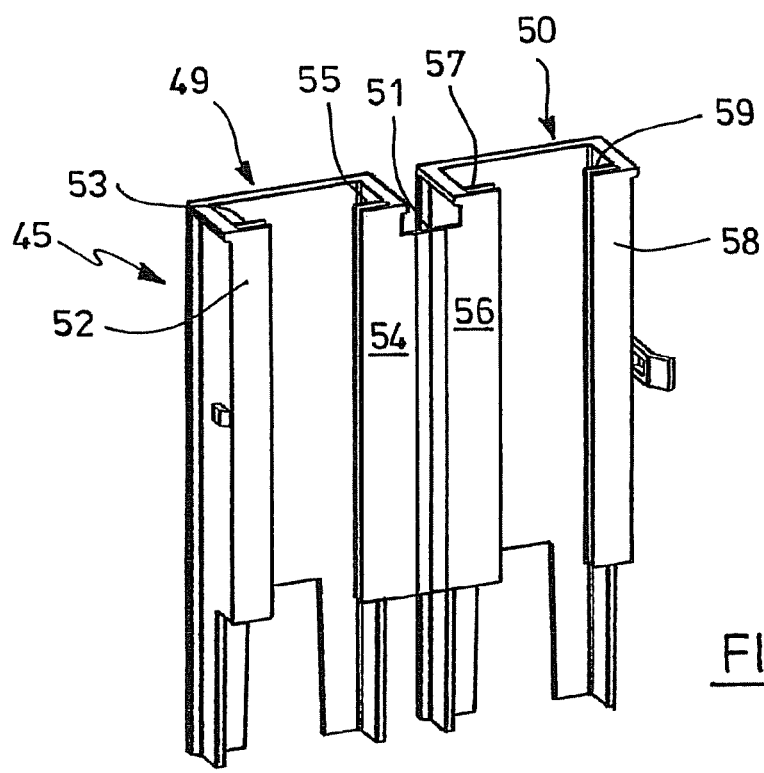
FIG. 10 an adapter for the receiving of two slides in an open state in a perspective view diagonally from the top and from the side.

While this invention may be embodied in many different forms, there are described in detail herein a specific preferred embodiment of the invention. This description is an exemplification of the principles of the invention and is not intended to limit the invention to the particular embodiment illustrated The cuvettes according to FIG. 1 through 4, 9 through 14 and 25 through 28 are not part of this application. They are only described for better visualization of the claimed invention.

In the following, the specifications "above" and "below" refer to the aligning that the concerned device parts have in the case of arrangement in a cuvette shaft of a photometer or spectrometer.

The cuvette shown in FIG. 1 through 4 consists of at least two parts.

A device 1 consisting of two plates 2, 3 with planar measuring surfaces 4, 5 on the inside and an adapter 6 for the positioning of the device 1 in a conventional photometer, spectrophotometer or the like.

In the example, the plates 2, 3 of the device 1 are arranged on the free ends of the arms 7, 8 of a pair of tweezers 9. The arms 7, 8 are beveled in the bottom area towards the plates 2, 3. The arms 7, 8 are preferably permanently connected with each other on the upper ends at 10. The arms 7, 8 can be pivoted together elastically. The ability to pivot the two arms 7, 8 together is restricted by spacers 11, 12 arranged on the insides of the arms 7, 8 in the form of two fins running diagonal to the arms in the vicinity of the measuring surfaces.

The adapter 6 itself has the rectangular profile of a standard cuvette. It is closed circumferentially in the top area 13 and has four feet 14 through 17 on the bottom.

The adapter 6 has a hollow space 18 inside, wherein two sets of parallel guide rails 19, 20, 21, 22 for the tweezers 9 are arranged on two opposing side walls. The pair of tweezers 9 can be inserted with arms pivoted together in accordance with FIG. 2 into the guide formed by the guide rails 19 through 22.

The guide rails 19 through 22 are restricted on the bottom by delimiting walls 23, 24, that are tilted inside, the tilt of which matches the tilt of the beveling of the arms 7, 8 of the tweezers 9. The delimiting walls 23, 24 protrude inside from the side walls, which carry the guide rails 19 through 22.

A box-shaped bottom part 25 is applied to the bottom edges of the delimiting walls 23, 24. It has passage openings 26, 27 on opposing front surfaces.

The construction of the adapter 6 thereby corresponds mainly with the cuvette in accordance with German patent DE 198 26 470 C1, U.S. Pat. No. 6,249,345, the disclosure of which is incorporated by reference. The deviations from the aforementioned construction consist in that the insides of the side walls are provided with guide rails 19 through 22 and the box-shaped bottom part 25 has passage openings 26, 27.

The pair of tweezers 9 can be disposable. The adapter 6 can also be disposable or reusable. Tweezers 9 and adapter 6 are preferably made of plastic.

A low volume of liquid to be analyzed is positioned between the optically transparent measuring surfaces 4, 5 of the device 1. The adapter 6 serves to subsequently position the device 1 with the planar measuring surfaces 4, 5 in vertical alignment in a cuvette shaft such that the measurement can be performed without further changes to the optical path in a conventional photometer or spectrometer.

The pair of tweezers 9 can have an insertion aid, which enables a simple "filling" of the measuring surfaces 4, 5. In the open state, the arms 7, 8 of the tweezers 9 are positioned with respect to each other such that a sufficiently large free space for the application of the sample, e.g. in the form of a drop, on one of the planar measuring surfaces 4, 5, is guaranteed. By pressing the two arms 7, 8 together, the planar measuring surfaces 4, 5 on the end of the arms 7, 8 are moved together so that the drop moistens both measuring surfaces 4, 5. The planar measuring surfaces 4, 5 can thereby be shaped and/or coated such that the expansion direction of the medium towards the measuring direction is aided and can only escape in one direction, e.g. upwards, in the case of an overdosage. Through the two spacers 11, 12, preferably near the planar measuring surfaces 4, 5, the arms 7, 8 are positioned such that a defined optical layer thickness is created between the measuring surfaces 4, 5. Measurements with volumes ranging from one microliter to several microliters can be realized in an adapter 6 by means of different tweezers 9 with different layer thicknesses.

The pair of tweezers 9 can also have a locking function, which makes it possible for the user to lay down the tweezers 9 in the closed state in that the spacers 11, 12 rest against each other.

Furthermore, the pair of tweezers 9 can also have alignment devices, which align the measuring surfaces 4, 5 parallel.

The pair of tweezers 9 is inserted in the closed state into the guide rails 19 through 22 of the adapter 6, until the beveling of the arms 7, 8 rests against the tilted delimiting walls 23, 24 of the adapter. In this position, the plates 2, 3 are arranged vertically in the adapter 6 and are aligned with the outsides on the passage openings 26, 27. The pair of tweezers 9 can be held in the closed state by the guide rails 19 through 22.

In the case of arrangement of the adapter 6 in the cuvette shaft of a photometer or spectrometer, the passage openings 26, 27 are arranged in the beam path of the measurement optics so that it can be used for the optical measurement of the sample between the measuring surfaces 4, 5.

The adapter 6 can be designed such that the liquid sample is prevented from escaping in the case of faulty handling e.g. vibration. It can also have an aperture character, whereby universal use independent of the spectrometer type is possible. The adapter 6 can be designed to be disposable like a cuvette, however replacement is only necessary in the case of faulty handling.

The cuvette according to FIG. 5 through 8 is made up of two parts, namely a measurement tip 28 and an adapter 29. The measurement tip 28 has a top end with a top opening 30, with which it can be clamped on a fastening appendage of an e.g. commercially available pipette. Furthermore, it has a bottom end with a bottom opening 31. The bottom opening 31 is restricted on the insides by a device 1 comprising two transparent plates 2, 3 with planar and preferably plane-parallel measuring surfaces 4, 5. The separation distance area between the plates 2, 3 is closed laterally so that the separation distance area is only open on the bottom at 31.

A continuous channel is designed in the measurement tip 28 between the top opening 30 and the bottom opening 31. On the outside, the measurement tip 28 has a tapered shape from top to bottom.

The adapter 29 is also box-shaped and fitted on a standard cuvette shaft. In the top area 32, it is closed on the perimeter and has four feet 33 through 36 on the bottom. On the inside, the adapter 29 has a hollow space 37, in which a receiver 38 is arranged. The receiver 38 is fit on the outer contour of the measurement tip 28. The receiver 38 is supported inside on the walls of the adapter 29 by radially running fins 39, 40, 41, 42.

The measurement tip 28 can be fitted on a fastening appendage of an e.g. commercially available pipette analogous to a conventional pipette tip, by means of which the medium to be measured can be absorbed between the plates 2, 3. The medium thereby moistens the planar measuring surfaces 4, 5. Through different measurement tips 28 with different separation distances between the measuring surfaces 4, 5, different sized measurement reservoirs for measurements with volumes ranging from under one microliter to several microliters (e.g. 0.5 to 5 microliters) or respectively different layer thicknesses can be realized in one cuvette. In particular in the case of the design for the measurement of very small volumes, the sample to be measured can already be pulled between the plates 2, 3 through capillary forces. The receiving of the sample with the help of an e.g. commercially available pipette is then not necessary.

The filled measurement tip 28 is inserted into the adapter 29 by means of a pipette. The shape of the receiver 38 adapts to the shape of the measurement tip 28 such that the inserted measurement tip with the plates 2, 3 is arranged in the free spaces between the feet 33 through 36. The measurement tip 28 can then be discharged from the pipette. But it can also remain connected with the pipette during the subsequent measurement. The cuvette 29 can then be inserted into a cuvette shaft with the inserted measurement tip 28 so that the optical path of the optical measuring device runs between opposing free spaces between each of the pairs of feet 33, 34 and 35, 36 and diagonally through the two plates 2, 3 and the sample located in it. The receiving of the sample is aided by hydrophilic surfaces.

The adapter 29 can be designed such that the liquid to be measured is prevented from escaping in the case of faulty handling—e.g. in the case of strong vibration. It can also serve as a guide for the correct alignment of the planar measuring surfaces 4, 5 with respect to the measuring direction of the photometer. Furthermore, it can have an aperture character, whereby universal use independent of the spectrometer type is possible.

The Measurement tip 28 and the adapter 29 can both be consumable. The measurement tip 28 can be replaced after each measurement. The replacement of the adapter 29 can be restricted to a case of faulty handling.

The next two exemplary embodiments comprise two hinged adapter parts, which are preferably undetachably interconnected via a joint. When folded together, the adapter parts form one adapter with the dimensions e.g. of a standard cuvette. The joint can be attached to the short or the long side of the device. When opened up, the sample to be measured is applied either to one or to both measuring surfaces.

The cuvette according to FIG. 9 through 12 comprises two plate-like sample carriers (slides) 43, 44 and an adapter 45. The sample carriers 43, 44 are identical. They have a broadened handle and path delimiter 47 on the top end of a lamellar middle part 46. On the bottom, the lamellar middle part 46 is conically tapered at 48. On the bottom end, the slides 43, 44 each have a plate 2, 3 with the planar measuring surface 4 or respectively 5 preferably on one side.

The adapter 45 comprises two adapter parts 49, 50, which are hinged together via an integral hinge 51. When folded together, the adapter parts 49, 50 form an adapter 45 according to FIG. 12, the shape of which mainly corresponds with that of adapter 6 according to FIGS. 3 and 4. However, in contrast to the adapter 6, the adapter 45 has in both adapter parts 49, 45 a complete guide made up of four guide rails 52 through 55 and 56 through 59.

The adapter 45 and the slides 43, 44 are preferably made of plastic.

Figure 11:
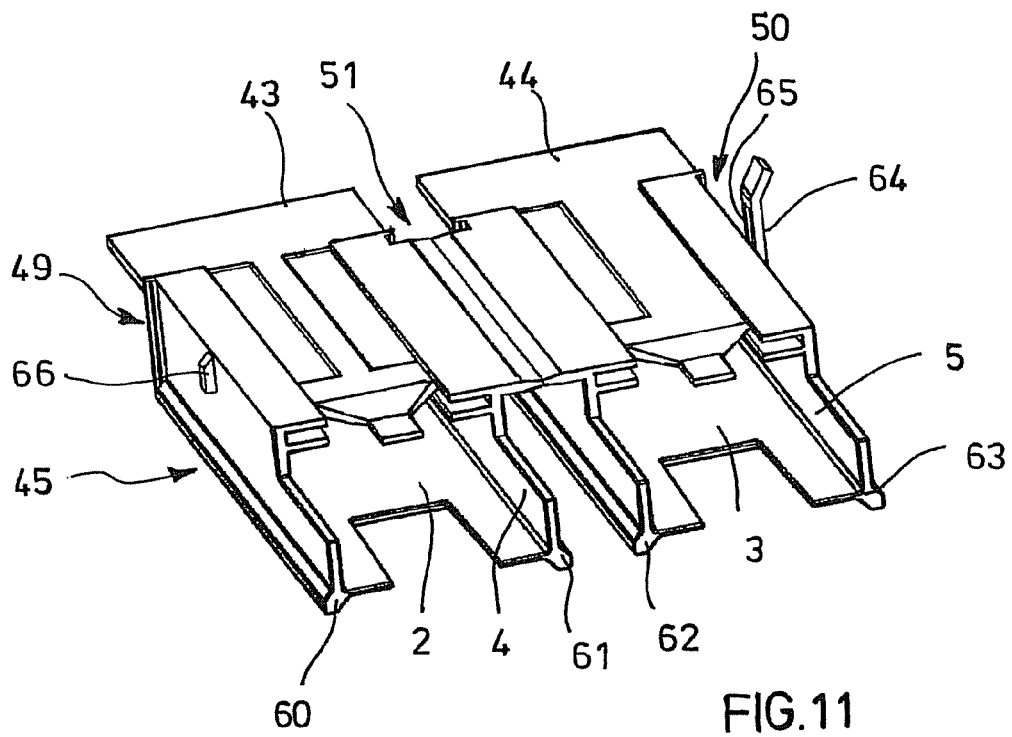
FIG. 11 the adapter populated with two slides in an folded-together state in a perspective view diagonally from the bottom and from the side.

According to FIG. 11, two slides 43, 44 are inserted into the guides 52 through 55 and 56 through 59, until the handle and the path delimiter 47 rest against the upper edge of the two adapter parts 49, 50. In this position, the plates 2, 3 are arranged in recesses between feet 60, 61 of the adapter part 49 and 62, 63 of the adapter part 50. Furthermore, a locking of the slides 43, 44 with the guides 52 through 55 and 56 through 59 can be provided.

A drop of the liquid to be measured is then applied to the planar measuring surface 4. The two adapter parts 49, 50 are then folded together, wherein the liquid comes in contact with the measuring surface 5.

The folded-together adapter parts 49, 50 are locked together by means of a locking hook 64 with a locking recess 65 on the adapter part 50 and a locking protrusion 66 on the adapter part 49. The locking hook 64 with its locking recess 65 is thereby pushed onto the locking protrusion 66. The lock can be released by pressing the locking hook 64 in the opposite direction.

Figure 12:
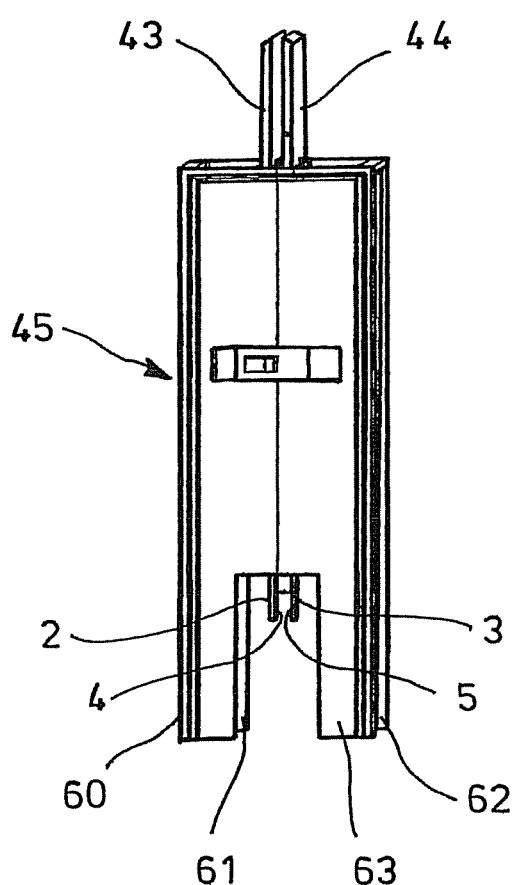
FIG. 12 the adapter populated with the slides in the closed state in a perspective view of two sides.
Figure 13:
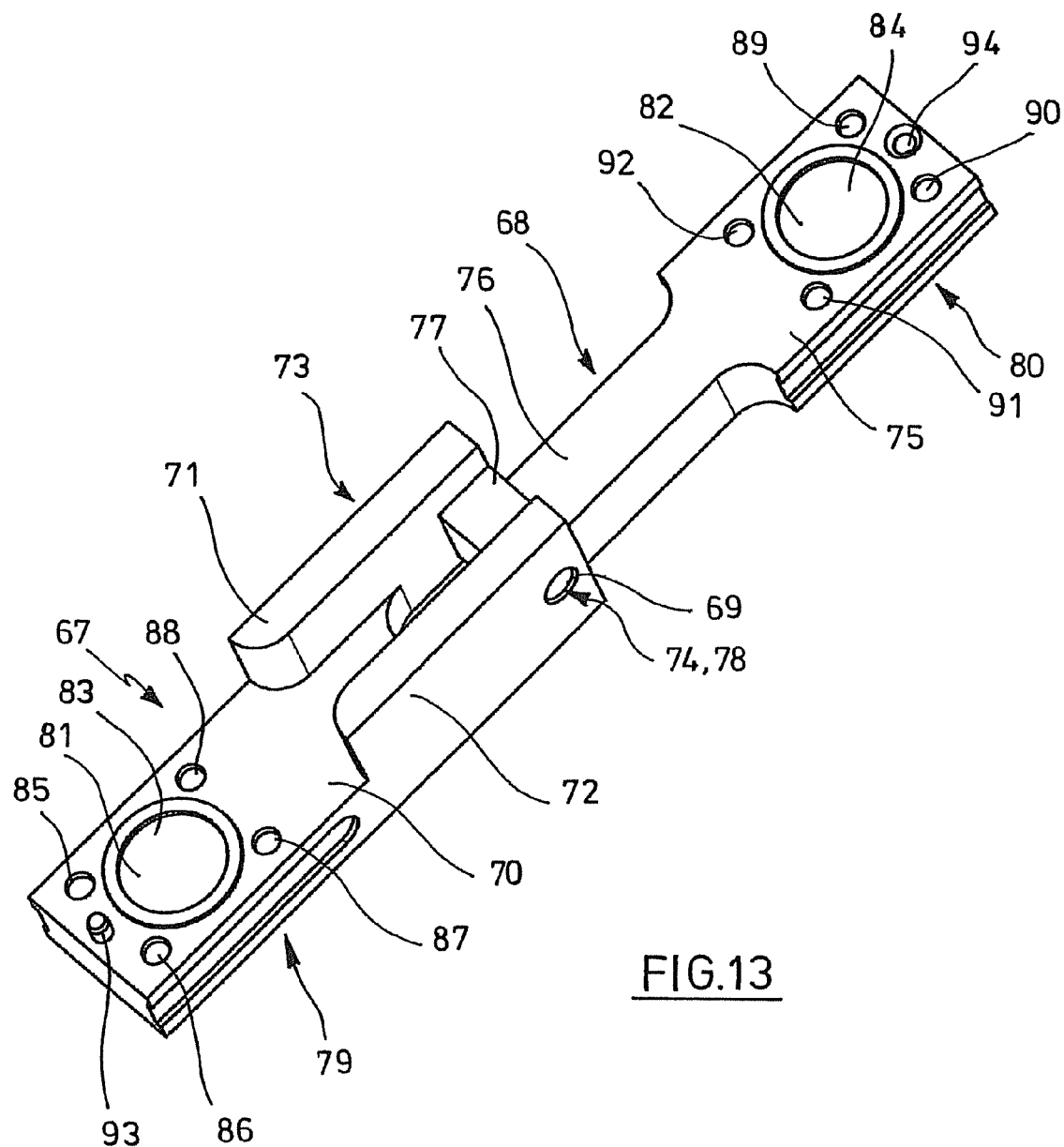
FIG. 13 an adapter populated with insert parts with planar measuring surfaces with adapter parts pivoted apart in a perspective view diagonally from the bottom and from one side.
Figure 14:
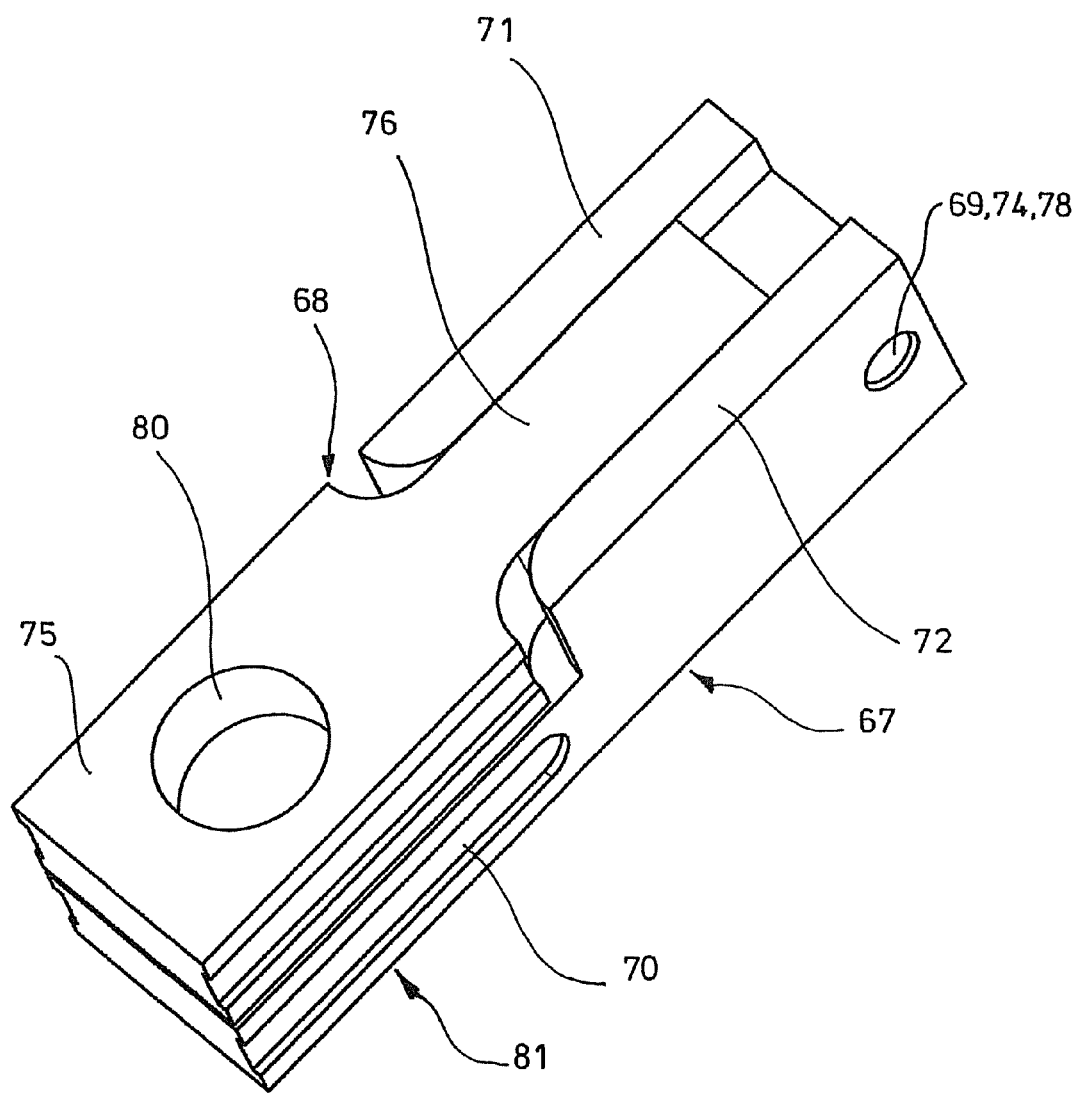
FIG. 14 the same adapter with adapter parts pivoted together in the same perspective view.

According to FIG. 12, the closed adapter 45 can be inserted into a standard cuvette shaft, wherein the beam path of the optical measuring device passes through the recesses between the feet 60, 61 and 62, 63 through the two plates 2, 3.

In the cuvette according to FIG. 9 through 12, the adapter parts 49, 50 are jointed together along a longitudinal side. In the cuvette according to FIGS. 13 and 14, the adapter parts 67, 68 have a hinged connection 69 along a diagonal axis.

For this, the adapter part 67 has a plate-like base part 70, which has two bars 71, 72 in the top area on one side on the outside. Bearing eyes 73, 74 of the swivel joint 69 are arranged in the bars 71, 72.

The adapter part 68 generally consists of a plate-like support part 75, which is connected with one end of a connecting arm 76, which supports a bearing block 77 on the other end. The bearing block 77 is arranged between the legs 71, 72, wherein an axis or shaft 78 passes through a central passage bore hole of the bearing block 77, which is held in the bearing eyes 73, 74 on both ends.

The base part 70 and the support part 75 have passage openings 79, 80, which are flush with each other in the folded-together state of the adapter parts 67, 68. Plate-like insert parts 81, 82 with planar measuring surfaces 83, 84 on the insides sit on the insides of the passage opening 79, 80.

The base part 70 and the support part 75 preferably each have magnets 85 through 88 and 89 through 92 inserted inside, each of which rest against each other in pairs in the folded-together state. Furthermore, a centering pin 93 protrudes from the base part 70, to which a centering receiver 94 of the support part 75 is assigned.

A sample can be applied to one or both planar boundary surfaces 81, 82 in the open state of the adapter. The adapter can be inserted into a standard cuvette shaft after folding together the adapter parts 67, 68. The light path of the optical measuring device passes through the passage openings 79, 80, the transparent plates 81, 82 arranged behind them and the sample located between them.

The inserts 81, 82 are e.g. made of UV-permeable quartz glass or UV-permeable plastic. If applicable, they are provided with a special surface structure.

The boundaries of the passage holes 80, 81 form apertures, which cause the measurement light of the photometer or spectrometer to only radiate the sample. The adapter parts 67, 68 are preferably made of plastic.

The adapter parts 67, 68 can be made of another material, for example metal, in particular if they are designated for reuse. In another variant, the adapter parts 67, 68 can be made of the same plastic as the insert parts 81, 82 and if applicable can be manufactured inseparably as an injection-molded part.

Figure 15:
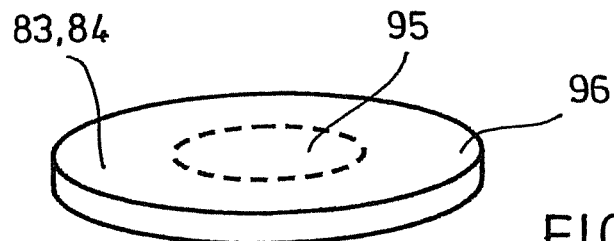
FIG. 15 insert part with planar measuring surface with liquid-moistening and liquid-repelling zones in a view diagonal to the planar measuring surface and to the side.
Figure 16:
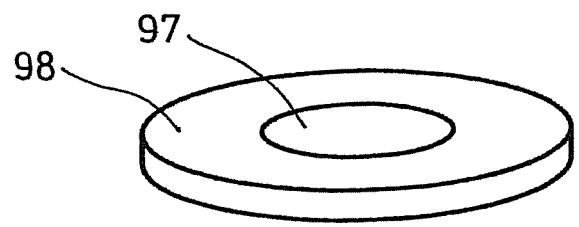
FIG. 16 the same insert part in a perspective view of the opposing planar outside.
Figure 17:
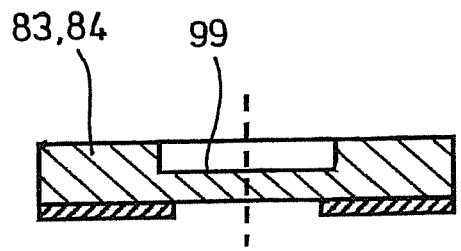
FIG. 17 planar measuring surface with recess in a longitudinal cut.
Figure 18:
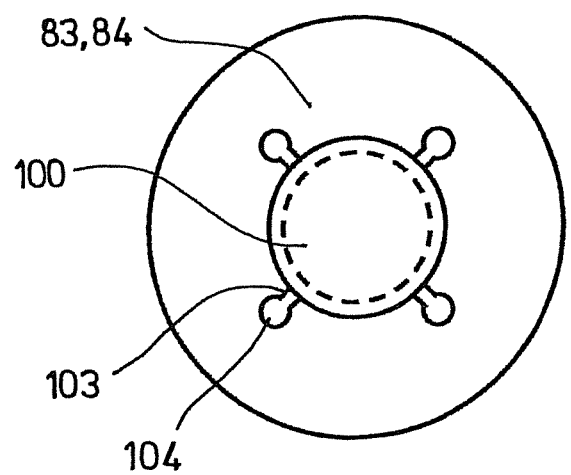
FIG. 18 planar measuring surface with several overflow chambers in a top view.
Figure 19:
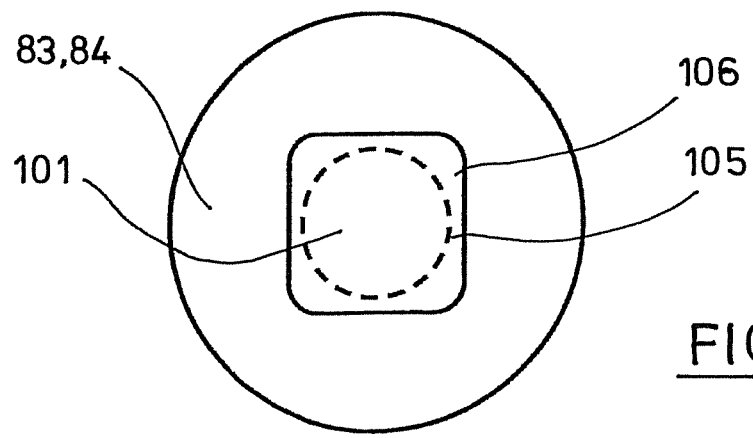
FIG. 19 planar measuring surface with an overflow chamber in a top view.
Figure 20:
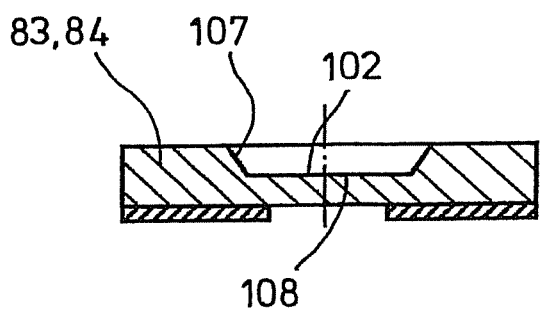
FIG. 20 planar measuring surface with a liquid-moistening central area and liquid-repelling boundary surfaces in a longitudinal cut.

According to FIGS. 15 and 16, the optically transparent measuring surfaces 83, 84 are designed in the center with a central liquid-moistening surface part 95, around which is located a liquid-repelling surface part 96. The liquid-moistening and liquid-repelling properties of the areas 95, 96 can be produced through coatings. There is no mechanical edge between the two surface parts 95, 96, which are disruptive during the cleaning of the measuring surfaces 83, 84. The measuring surfaces 83, 84 are cleaned from the surface part 95 up to the surface part 96 so that no residual impurities remain in the central surface part 95.

A translucent surface part 97 corresponds to the liquid-moistening surface part 95 and an opaque surface part 98 on the outside of the insert 83, 84 corresponds to the liquid-repelling surface part.

The surface parts 95, 96 restrict the spreading of the liquid sample on the measuring surfaces 83, 84. The liquid drop has a large contact angle point on the liquid-repelling or respectively hydrophobic surface part. As a result, it protrudes high above the measuring surfaces 83, 84. In the liquid-moistening or respectively hydrophilic surface part 95, the drop is in contrast held tight or respectively anchored. As a result, no flat but approximately hemispherical liquid drops are created so that, during the folding together of the adapter parts 67, 68, a drop applied to a measuring surface 83 or 84 securely moistens the other measuring surface 84, 83 or drops applied to both measuring surfaces 83, 84 are securely unified. As a result, a defined liquid column is created and thus a defined measuring length or respectively layer thickness.

The plates 2, 3 of the other exemplary embodiments can be designed accordingly on the measuring surfaces 4, 5 and the outsides.

In the exemplary embodiments according to FIGS. 17 through 20, differently shaped recessed 99, 100, 101, 102 are arranged in the measuring surfaces 83, 84. The recesses 99 through 102 receive samples and restrict their spreading on the measuring surfaces 83, 84. According to FIGS. 18 and 19, excess sample amounts can escape via radial channels 103 in reservoir chambers 104 or via an overflow edge 105 into an overflow chamber 106. In the exemplary embodiment in FIG. 20, the recess 102 expands outward conically. Moreover, the boundary surface 107 restricting the spreading can be liquid-repelling and the base surface 108 liquid-moistening so that the drop protrudes as far as possible from the measuring surface 83, 84.

In order to restrict the spreading of the drop, a planar platform with a small surface can also be arranged on the measuring surface 83, 84. The planar platform prevents the expansion of the drop due to its surface tension. This causes an increase in the drop height and a reduction in the required sample amount can be achieved.

The design of the measuring surfaces according to FIG. 17 through 20 or with a platform can be achieved in all exemplary embodiments.

Figure 21:
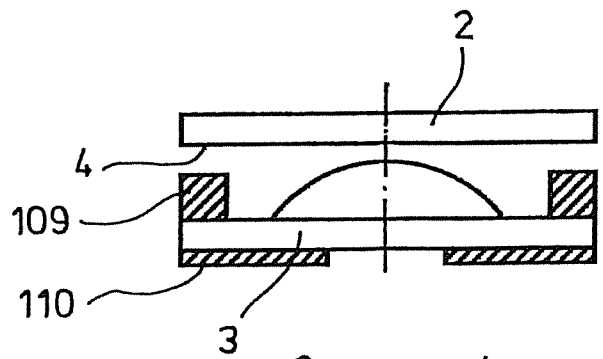
FIG. 21 planar measuring surfaces with an applied drop before convergence of the measuring surfaces in a longitudinal cut.
Figure 22:
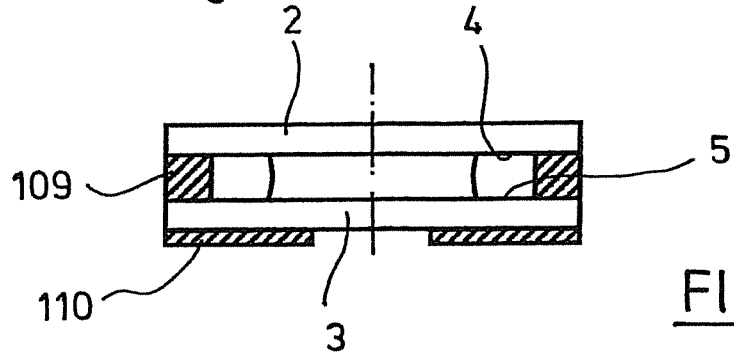
FIG. 22 the same measuring surfaces after convergence in a longitudinal cut.

According to FIGS. 21 and 22, the thickness of the layer between the two measuring surfaces 4, 5 can be defined by a spacer 109. An aperture 110 is applied to the outside of the plate 3 as a coating.

In this example, a drop is only applied to measuring surface 5, which moistens the measuring surface 4 when placed on the spacer 9.

Figure 23:
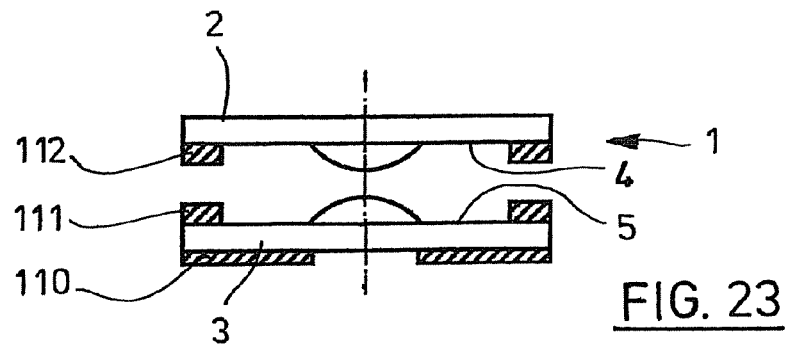
FIG. 23 two planar measuring surfaces with two applied drops before convergence of the measuring surfaces in a longitudinal cut.
Figure 24:
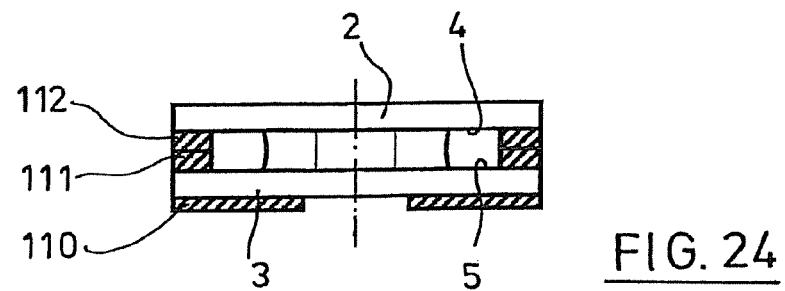
FIG. 24 the same measuring surfaces after convergence in a longitudinal cut.

In the exemplary embodiment according to FIGS. 23 and 24, spacers 111, 112 are assigned to both measuring surfaces 4, 5, which come in contact with each other when the device is closed. In this example, the layer thickness is defined by both distance rings 111, 112. Furthermore, the application of drops on both measuring surfaces 4, 5, which flow together when device 1 is closed, is shown.

Figure 25:
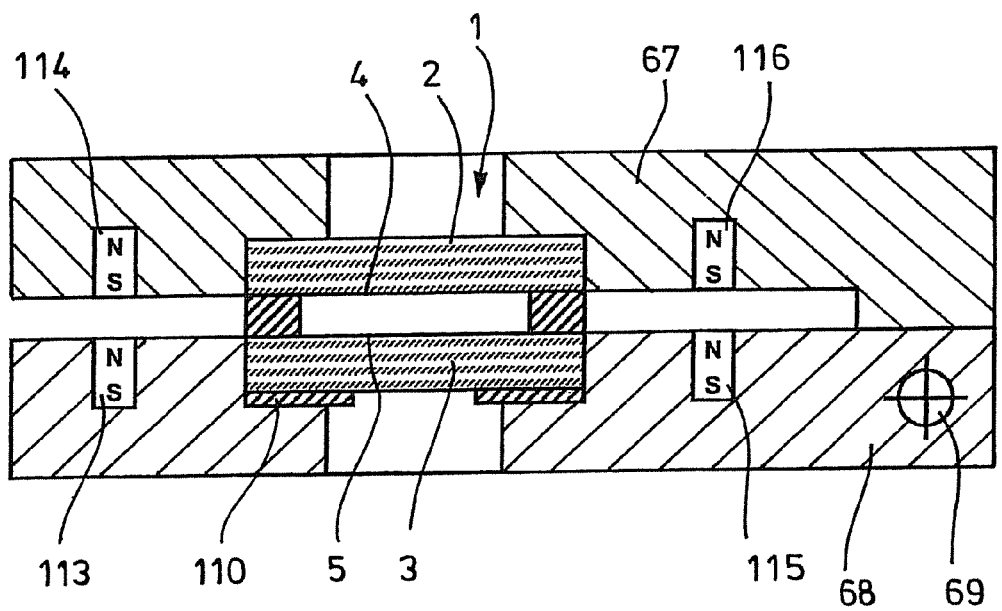
FIG. 25 magnetic locking of two measuring surfaces in measurement position in a longitudinal cut.

The exemplary embodiment in FIG. 25 differs from that according to FIGS. 21 and 22 in that the defined layer thickness is preferably guaranteed by magnetic forces of magnets 113, 114, 115, 116, the opposite poles of which are arranged at a short distance from each other when device 1 is closed. The magnets 113 through 116 are integrated in device parts (e.g. adapter parts 67, 68) of the cuvette, which receive the inserts 2, 3.

So that the plane parallelism of the measuring surfaces 4, 5 is guaranteed, a joint 69 designed between the device parts 67, 68 can be designed floating so that the system is not geometrically overdetermined. In the closed state, the measured material is positioned definitively, securely and stable in the flap cuvette with the two adapter parts 67, 68.

Another embodiment of the invention represents a storage of the one-time parts (not shown individually). The inserts 2, 3 for one-time use can be inserted easily from an easily manageable magazine preferably in the form of a cartridge into the openings provided for this in a reusable flap cuvette. After use, the one-time inserts 2, 3 are pushed out of the foldable adapter and thrown away by hand or by means of a device or by means of an appendage on the cartridge. New inserts 2, 3 can then be inserted again.

The one-time parts can also be combined with two-part adapters designed as a one-time part. Furthermore, a combined one-time part with front and rear part made of a tool, if applicable also as a so-called two-component, injection-molded part is possible.

Figure 26:
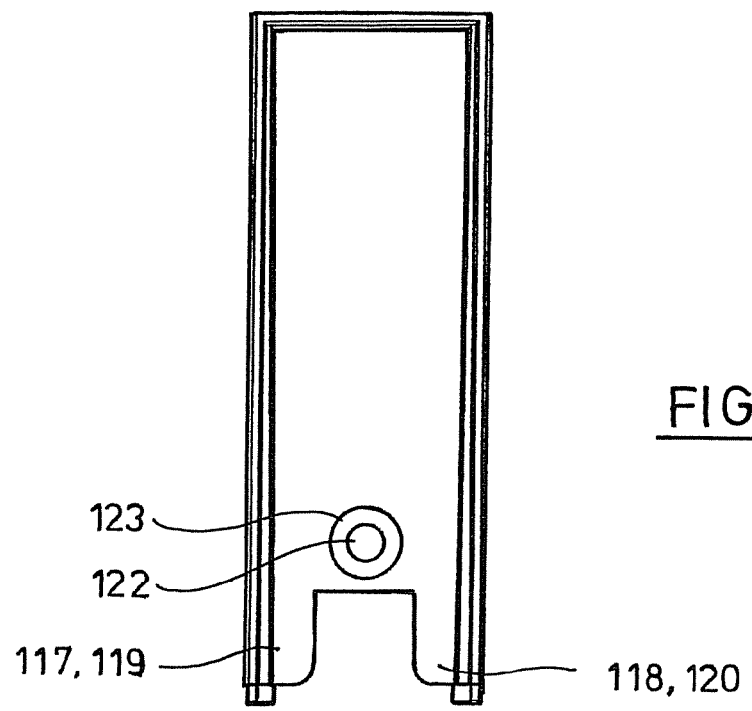
FIG. 26 cuvette with a capillary channel open on two sides in a side view.
Figure 27:
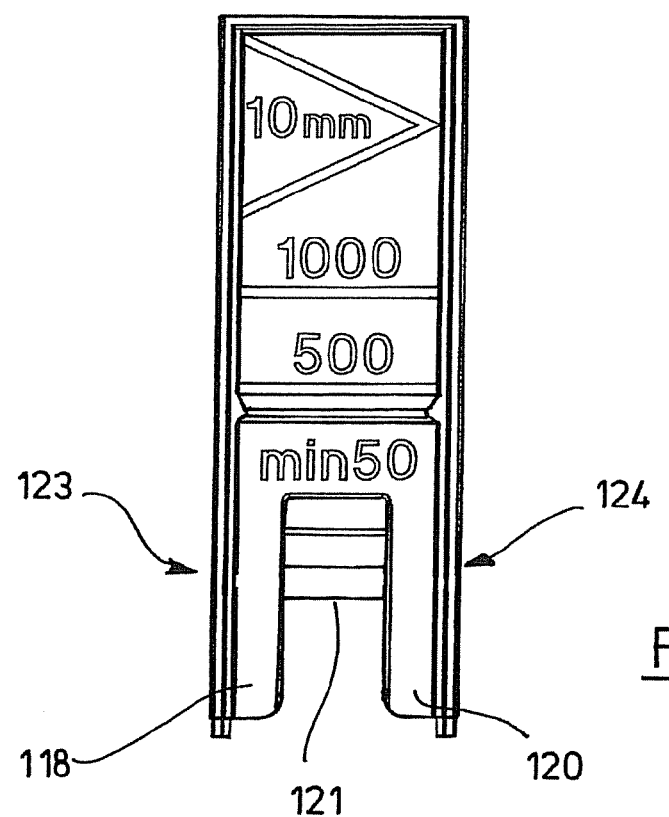
FIG. 27 the same cuvette in another side view.
Figure 28:
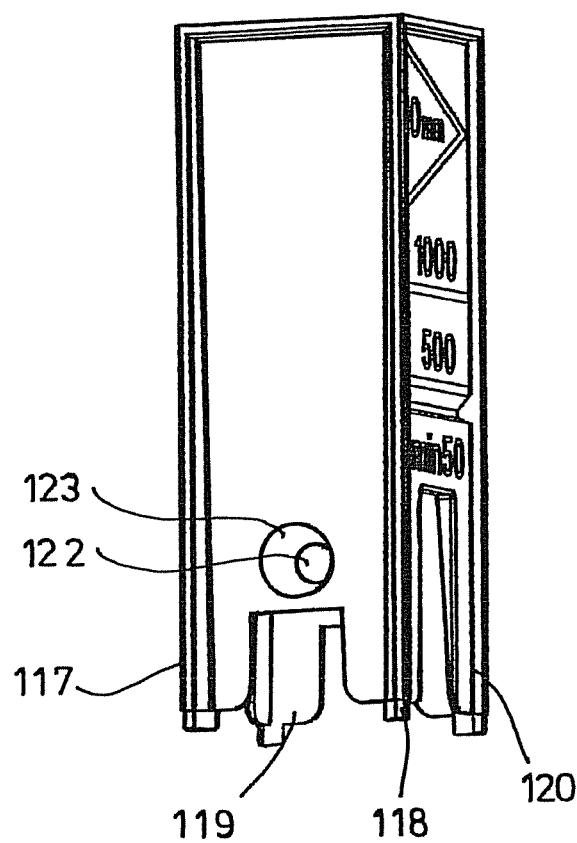
FIG. 28 the same cuvette in a perspective view diagonally from two sides.

The cuvette according to FIG. 26 through 28 mainly correspond with the cuvette according to the exemplary embodiment in DE 198 26 470 C1, which is included through reference. However, in contrast to the aforementioned cuvette, the box-shaped bottom part 121 arranged between the four feet 117, 118, 119, 120 is not open inside towards a hollow space of the cuvette, but is rather closed. Furthermore, a channel 122 open on both sides, which has funnel-shaped extensions 123, 124 on both outsides, runs through this bottom part 121.

The cuvette has the shape of a commercially available cuvette so that it can be inserted into a commercially available photometer or respectively spectrometer.

Optical measurements can be performed through the channel 122 open on both sides. During a measurement, no light is thereby directed through a plastic wall of the cuvette and the measurement is thus not impacted. A blank value measurement for each cuvette is not required.

The channel 122 conically expands to the outsides of the cuvette so that its overdosage causes an insignificant increase in the optical layer thickness. As a side effect, the cuvette thus receives insertion aid. A pipette tip can be applied to the extensions 123, 124 and the channel 122 can be filled until the liquid escapes from the border between the conical and cylindrical area of the channel 122. The liquid now fills the channel 122 completely and is held therein by adhesion or respectively capillary effect.

The conical extensions 123 can be roughened on one hand in order to achieve an aperture effect and on the other hand in order to prevent the liquid from escaping during improper handling. Additionally, a tray can then be provided below the channel 122, which can receive the escaping liquid. Since the channel 122 is considerably shorter than the overall width of the cuvette, the liquid can only fall into this tray.

The exemplary embodiments serve for better visualization of the invention. The invention in not limited to the exemplary embodiments.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A cuvette comprising at least one insert (28) with two measuring surfaces (4, 5), wherein the insert is a pipette tip (28), which has the two measuring surfaces (4, 5) on one end, which is distanced from another end (30) of the pipette tip (28), which is designed for connection with a pipette, and an adapter (29) for insertion in a cuvette shaft of an optical measuring device and an accommodation for releasably holding the at least one insert in the adapter (29) with the measuring surfaces (4, 5) at a separation distance from each other for the positioning of a sample between the measuring surfaces (4, 5) in a beam path of the optical measuring device passing through the cuvette shaft.

2. The cuvette according to claim 1 with means for the positioning of the measuring surfaces (4, 5) in a standard cuvette shaft.

3. The cuvette according to claim 1 with means for the positioning of the measuring surfaces (4, 5) in different positions in a cuvette shaft.

4. The cuvette according to claim 3 with means for the positioning of the measuring surfaces (4, 5) in different height positions in a cuvette shaft.

5. The cuvette according to claim 1, in which the accommodation for the releasable holding comprises a receiver (38) of the adapter (29) and a contour of the measurement tip (28), the geometries of which are set for each other such that the measurement tip (28) can be inserted into the receiver (38) in a certain position.

6. The cuvette according to claim 1, in which the two measuring surfaces (4, 5) are optically transparent.

7. The cuvette according to claim 1, in which the two measuring surfaces (4, 5) are plate-like.

8. The cuvette according to claim 1, in which the insert (28) and/or the adapter (29) are made of plastic and/or metal.

9. The cuvette according to claim 1, in which at least one measuring surface (4, 5) is hydrophilic.

10. The cuvette according to claim 1, in which the two measuring surfaces (4, 5) are planar.

11. The cuvette according to claim 1, in which the measuring surfaces (4, 5) in the measurement position are arranged parallel.

12. The cuvette according to claim 1, in which the separation distance of the measuring surfaces (4, 5) from each other is maximum 2 mm preferably approximately 1 mm.

13. The cuvette according to claim 1, in which the separation distance of the measuring surfaces (4, 5) from each other is measured such that samples with a volume of approximately 0.5 to 5 microliters can be held in between.

14. The cuvette according to claim 1, which has at least one aperture for restricting a light beam through the measuring surfaces (4, 5).

15. The cuvette according to claim 14, in which the adapter (29) has the aperture.

16. An insert for an adapter (29) insertable in a cuvette shaft of an optical measurement device, wherein the insert (28) has two measuring surfaces (4, 5) and accommodation member for the releasable holding on the adapter (29) with the measuring surfaces (4, 5) at a separation distance from each other for the positioning of a sample between the measuring surfaces (4, 5) in a beam path of the optical measurement device passing through the cuvette shaft and wherein the insert is a pipette tip (28), which has the two measuring surfaces (4, 5) on one end, which is distanced from another end of the pipette tip (28), which is designed for connection with a pipette.

17. The insert according to claim 16, wherein the insert is a pipette tip (28), which has the two measuring surfaces (4, 5) on one end, which is distanced from another end (30) of the pipette tip (28), which is designed for connection with a pipette, and an adapter (29) for insertion in a cuvette shaft of an optical measuring device and accommodation member for releasably holding the at least one insert in the adapter (29) with the measuring surfaces (4, 5) at a separation distance from each other for the positioning of a sample between the measuring surfaces (4, 5) in a beam path of the optical measuring device passing through the cuvette shaft.

18. An adapter for at least one insert with two measuring surfaces, wherein the insert is a pipette tip (28), which has the two measuring surfaces (4, 5) on one end, which is distanced from another end of the pipette tip (28), which is designed for connection with a pipette, and wherein the adapter (29) can be inserted in a cuvette shaft of an optical measuring device and has an accommodation member for releasably holding the at least one insert (28) with the measuring surfaces (4, 5) at a separation distance from each other for the positioning of a sample between the measuring surfaces in a beam path of the optical measuring device passing through the cuvette shaft.

19. The adapter according to claim 18, wherein the insert is a pipette tip (28), which has the two measuring surfaces (4, 5) on one end, which is distanced from another end (30) of the pipette tip (28), which is designed for connection with a pipette, and an adapter (29) for insertion in a cuvette shaft of an optical measuring device and an accommodation member for releasably holding the at least one insert in the adapter (29) with the measuring surfaces (4, 5) at a separation distance from each other for the positioning of a sample between the measuring surfaces (4, 5) in a beam path of the optical measuring device passing through the cuvette shaft.

* * * * *